United States Patent
Ma et al.

(10) Patent No.: US 10,513,587 B2
(45) Date of Patent: Dec. 24, 2019

(54) SELF-INTEGRATING HYDROGELS AND METHODS FOR MAKING THE SAME

(71) Applicant: THE REGENTS OF THE UNIVERSITY OF MICHIGAN, Ann Arbor, MI (US)

(72) Inventors: Peter X. Ma, Ann Arbor, MI (US); Sen Hou, Beijing (CN)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/720,430

(22) Filed: Sep. 29, 2017

(65) Prior Publication Data

US 2018/0094106 A1 Apr. 5, 2018

Related U.S. Application Data

(63) Continuation of application No. PCT/US2016/025637, filed on Apr. 1, 2016.

(60) Provisional application No. 62/142,256, filed on Apr. 2, 2015.

(51) Int. Cl.
| | | |
|---|---|---|
| *C08J 3/075* | (2006.01) | |
| *C08J 3/24* | (2006.01) | |
| *A61K 35/28* | (2015.01) | |
| *A61K 35/32* | (2015.01) | |
| *C07D 239/47* | (2006.01) | |
| *C08F 271/02* | (2006.01) | |

(52) U.S. Cl.
CPC ............... *C08J 3/075* (2013.01); *A61K 35/28* (2013.01); *A61K 35/32* (2013.01); *C07D 239/47* (2013.01); *C08F 271/02* (2013.01); *C08J 3/24* (2013.01); *C08J 2205/022* (2013.01); *C08J 2301/02* (2013.01); *C08J 2305/02* (2013.01); *C08J 2305/08* (2013.01); *C08J 2329/04* (2013.01)

(58) Field of Classification Search
CPC .................. A61L 27/52; C08B 37/0021; C08J 2205/022; C08J 2300/14; C08J 2305/02; C08L 5/02
See application file for complete search history.

(56) References Cited

U.S. PATENT DOCUMENTS

2008/0260795 A1 10/2008 Baughman et al.

FOREIGN PATENT DOCUMENTS

| WO | WO 2006/118460 | 11/2006 |
|---|---|---|
| WO | WO 2012/168392 | 12/2012 |

OTHER PUBLICATIONS

Chen, Y. et al. "Moldable high internal phase emulsion hydrogel objects from non-covalently crosslinked poly(N-isopropylacrylamide) nanogel dispersions" Chem. Commun., 2013, 49, 1524-1526 (Year: 2013).*
Song, F. et al. "Using hydrophilic polysaccharide to modify supramolecular hydrogel from a low-molecular-mass gelator" Materials Science and Engineering C 30 (2010) 804-811 (Year: 2010)*
DeGreef, T.F.A. "Supramolecular polymers" Nature 2008, 453, 8, 171-173 (Year: 2008).*
International Search Report and Written Opinion for International Application No. PCT/US2016/025637 dated Jun. 21, 2016, 11 pages.
Cui, J. et al. "Multivalent H-bonds for self-healing hydrogels." Chemical Communications, 2012, vol. 48, pp. 9302-9304.
Ramaekers, M. et al. "Self-assembly of chiral supramolecular ureidopyrimidinone-based poly (ethylene glycol) polymers via multiple pathways." Macromolecules, 2014, vol. 47, pp. 3823-3828.
Kieltyka, R. E. et al. "Mesoscale modulation of supramolecular ureidopyrimidinone-based poly (ethylene glycol) transient networks in water." Journal of the American Chemical Society, 2013, vol. 135, pp. 11159-11164.
Guo, M. et al. "Tough stimuli-responsive supramolecular hydrogels with hydrogen-bonding network junctions." Journal of the American Chemical Society, 2014, vol. 136, pp. 6969-6977.
Hou, S. et al. "Rapid self-integrating, injectable hydrogel for tissue complex regeneration." Advanced Healthcare Materials, 2015, vol. 4, pp. 1491-1495 (E-pub. Jul. 15, 2015).

* cited by examiner

*Primary Examiner* — Andrew S Rosenthal
(74) *Attorney, Agent, or Firm* — Dierker & Kavanaugh, P.C.

(57) ABSTRACT

A self-integrating hydrogel includes a water-soluble polymer. The water-soluble polymer includes a repeating unit having at least one functional group that includes an oxygen atom, a sulfur atom, or a nitrogen atom, and a pendant chain covalently attached to the oxygen atom, the sulfur atom, or the nitrogen atom of the at least one functional group of the repeating unit. The pendant chain includes ureido-pyrimidinone.

10 Claims, 7 Drawing Sheets

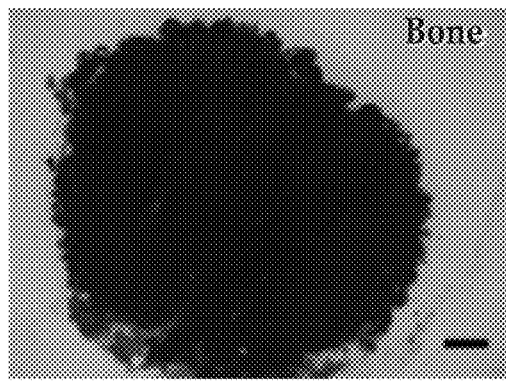
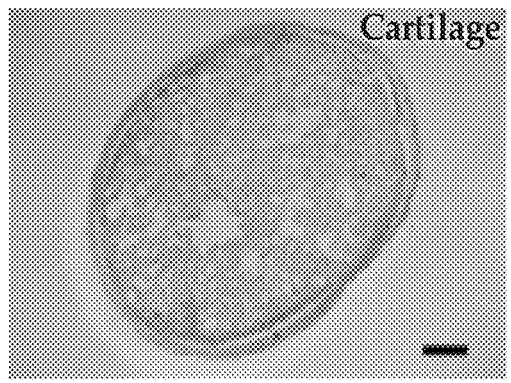
FIG. 9A  FIG. 9B
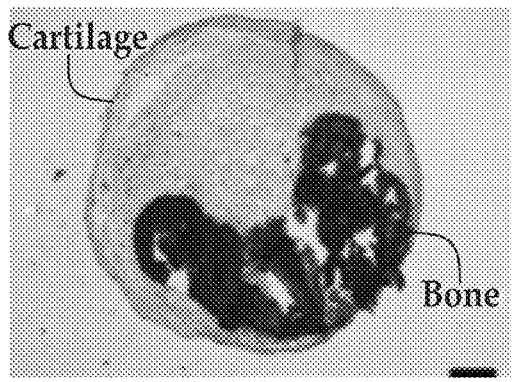
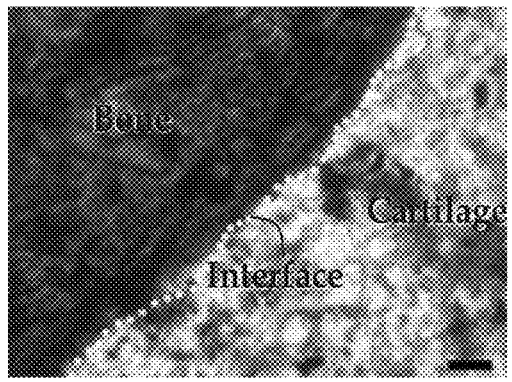
FIG. 9C  FIG. 9D
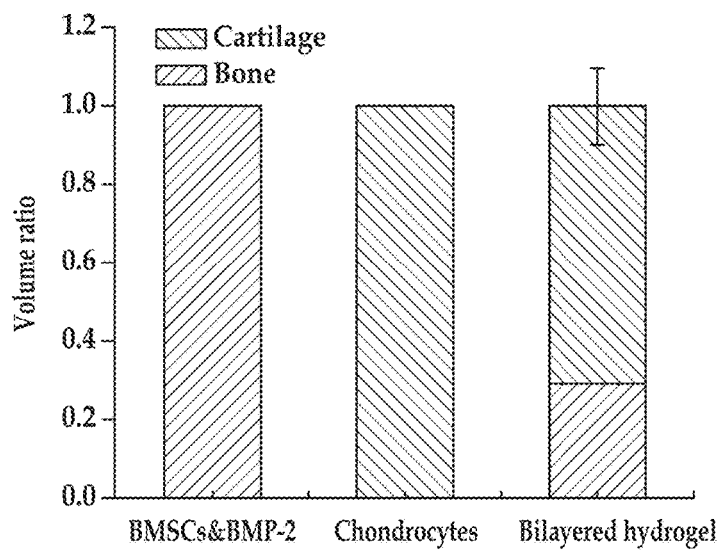
FIG. 9E

SELF-INTEGRATING HYDROGELS AND METHODS FOR MAKING THE SAME

CROSS-REFERENCE TO RELATED APPLICATIONS

This application is a continuation of co-pending international application S.N. PCT/US2016/025637, filed Apr. 1, 2016, which itself claims the benefit of U.S. Provisional Application Ser. No. 62/142,256, filed Apr. 2, 2015, each of which is incorporated by reference herein in its entirety.

STATEMENT REGARDING FEDERALLY SPONSORED RESEARCH OR DEVELOPMENT

This invention was made with government support under DE022327 awarded by the National Institutes of Health (NIH). The government has certain rights in the invention.

BACKGROUND

Regenerative medicine techniques often utilize scaffolding materials, which can serve the role of three-dimensional (3D) templates, and/or drug carriers, which can serve the role of a drug delivery mechanism. Tissue regeneration may be a potential treatment for patients with lost or diseased tissues. However, the regeneration of tissue complexes that consist of more than one type of tissue presents a challenge to tissue engineers.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 5A is a frequency spectra of the dynamic moduli of DEX-Upy hydrogels (DS 5.5) with concentrations of 12.5% and 10% w/w, FIG. 5B illustrates the dynamic modulus of the hydrogel (DS 5.5, 10% w/w) under increasing stress, FIG. 5C illustrates the dynamic modulus of the hydrogel (DS 5.5, 10% w/w) under cyclic high (100 Pa) and low (0.1 Pa) stresses as a function of time (in seconds), FIG. 5D illustrates the change of the dynamic modulus of the hydrogel (DS5.5, 10% w/w) with temperature;

FIGS. 9A-9E illustrate results of the subcutaneous implantation of the cell-gel constructs, where FIG. 9A is a black and white photograph of a section of a BMSCs/BMP-2 (bone morphogenetic protein) only group stained with Alizarin red (positive staining represents mineralized bone tissue), FIG. 9B is a black and white photograph of a section of a chondrocytes only group stained with Alcian blue (positive staining represents cartilage tissue), FIG. 9C is a black and white of a section of a self-integrated group with both chondrocytes and BMSCs/BMP-2 stained with both Alizarin red and Alcian blue, FIG. 9D is a magnified black and white image of the interface region of FIG. 9C, and FIG. 9E is a graph illustrating the quantification of bone and cartilage volumes using an image analysis software (Adobe Photoshop);

DETAILED DESCRIPTION

Figure 1A:
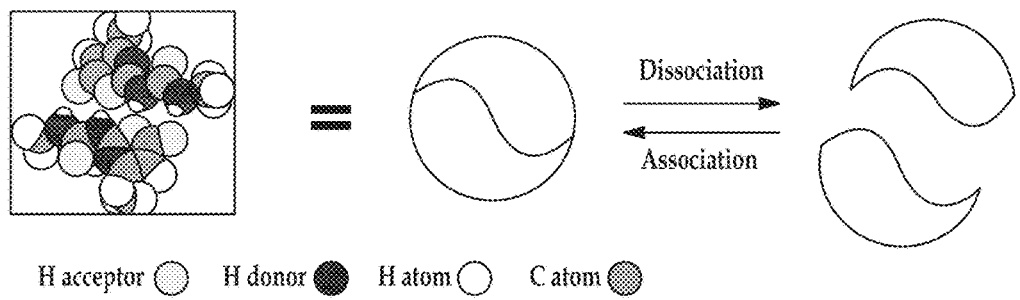
FIG. 1A is a schematic illustration of the quadruple hydrogen bonding of ureido-pyrimidinone, and the dissociation and association of the ureido-pyrimidinone.

Disclosed herein are self-integrating hydrogels that may be used in a variety of applications, including tissue engineering, drug delivery, tissue bulking, adhesive, cosmetics, wound dressing, and surgical dressing. Single tissues or multi-tissue complexes may by regenerated using the hydrogels disclosed herein. After having the appropriate cell(s) and/or biomolecule(s) incorporated/encapsulated therein, the hydrogel can self-integrate under mild conditions. This enables the regeneration of tissue (in some instances, multiple types of tissue) in spatially defined regions and also the seamless integration of the tissue(s). Some of the examples provided herein illustrate the regeneration of bone-cartilage tissue complexes, which resemble native tissue integration. However, the applications for the self-integrating hydrogels are not limited to these examples, and that the self-integrating hydrogels have potential for engineering various tissue complexes.

The self-integrating hydrogels disclosed herein are supramolecular hydrogels that are capable of self-assembling via cooperative and highly specific physical interactions. However, the hydrogels disclosed herein are not equivalent to a cooperative assembly of small peptides into a larger nanostructure. Rather, the supramolecular hydrogels disclosed herein are formed of a water-soluble polymer that includes a repeating unit and a pendant chain covalently attached to the repeating unit. The repeating unit is a biocompatible monomer or comonomer, and the pendant chain includes a unit with multiple hydrogen bonds. The multiple-hydrogen-bond along the backbone chain provides the water-soluble polymer with the capability to form strong, yet reversible interactions. The transient nature of the strong, yet reversible, interactions provides the water-soluble polymer with the ability to self-heal, self-integrate or self-recover without any external stimulus or intervention. With this property, separate hydrogel pieces, which may be carrying a respective type of cell and/or signaling biomolecule, can integrate to form the structure of a particular tissue complex.

In addition, the combination of the biocompatible monomer and the multiple-hydrogen-bond unit pendant chain provides the supramolecular hydrogel with a shear-thinning property (i.e., viscosity decreases with an increasing rate of shear stress), as evidenced by the yielding behavior in the rheological measurements disclosed herein. The shear-thinning property contributes to the supramolecular hydrogel being injectable (e.g., via a syringe). Since the hydrogels are injectable, they do not need to be pre-shaped or surgically implanted. Furthermore, the ability to be injected renders the hydrogel suitable for filling irregular tissue defects, such as tooth defects, fractured bone wounds, worn/diseased cartilage, and various soft tissues, such as intervertebral disc, spinal cord, brain, etc.

With both the shear-thinning property and the self-integrating property, the supramolecular hydrogel, which is in a gel state before injection, can be injected and then instantly recover to the gel state after injection.

As mentioned above, the hydrogel is formed of a water-soluble polymer, which includes a repeating unit and a pendant chain covalently attached to the repeating unit. Generally, the water-soluble polymer may be a modified dextran, a modified poly(vinyl alcohol), a modified chitosan, a modified cellulose, or some other water-soluble polymer that is modified with the pendant group disclosed herein. The water-soluble polymer is a multi-functionalized polymer because of the pendant groups attached to each repeating unit.

The repeating unit has at least one functional group. The functional group may be any functional group that is capable of reacting with an isocyanate or with another functional group that is attached to an isocyanate in order to covalently bind the pendant group (which includes the isocyanate) thereto. As examples, the functional group of the repeating unit includes an oxygen atom, a sulfur atom or a nitrogen atom. In the modified water-soluble polymer, the oxygen atom, sulfur atom, or nitrogen atom covalently attaches the pendant chain to the repeating unit. Examples of the repeating unit include glucose unit(s), vinyl alcohol, D-glucosamine, two β(1→4) linked D-glucose units, or another repeating unit that forms a water-soluble backbone and include a suitable functional group for covalently attaching the pendant chain.

In the examples disclosed herein, the pendant chain includes ureido-pyrimidinone. In some examples, the ureido-pyrimidinone is covalently linked to the oxygen, sulfur, or nitrogen atom of the repeating unit through an isocyanate. In other examples, the ureido-pyrimidinone is covalently linked to the oxygen, sulfur, or nitrogen atom of the repeating unit through another functional group. In these other examples, the ureido-pyrimidinone is attached to an isocyanate that has been reacted with another functional group, such as a hydroxyl group, an amine group, a thiol group, etc. This reaction generates an end group of the pendant chain that is capable of covalently attaching to the oxygen, sulfur, or nitrogen atom of the repeating unit. Other than isocyanate, functional groups such as activated esters, epoxy groups and acyl chloride groups can also be used for the attachment of the ureido-pyrimidinone.

Ureido-pyrimidinone is a multiple-hydrogen bond unit. More particularly, ureido-pyrimidinone is a quadruple hydrogen-bond array, which has a much higher bonding strength than a single hydrogen bond. FIG. 1A is a schematic illustration of the multiple hydrogen bonds of ureido-pyrimidinone (far left of FIG. 1A) and their dynamic interactions, including dissociation and association.

The strength of the interactions may also affect the erosion properties of the hydrogels as such hydrogels erode or degrade through dissociation of the reversible interactions. Strong supramolecular interactions behave similarly to covalent bonds, which are not susceptible to physical erosion. The ureido-pyrimidinone multiple hydrogen bond interactions provide the hydrogel with an appropriate erosion property, and thus a biomolecule release profile.

The hydrogels disclosed herein may be formed via a mild fabrication process, which does not utilize toxic components or non-physiological pH conditions. The mild fabrication process uses gentle solvents, such as water, PBS, etc. and physiological pH conditions ranging from 6 to 8. The ureido-pyrimidinone-containing pendant groups are grafted to the repeating units of the water-soluble polymer through a reaction with the functional group including the oxygen atom, the sulfur atom, or the nitrogen atom. In some examples of the method, the ureido-pyrimidinone is first attached to an isocyanate, which in turn is grafted to the repeating unit functional group, which includes the oxygen, sulfur, or nitrogen atom.

As one example of the method for forming the hydrogel, ureido-pyrimidinone-containing pendant groups may first be formed by attaching ureido-pyrimidinone to an isocyanate. The selected water soluble polymer may be dissolved in a solvent to form a solution. The ureido-pyrimidinone-containing pendant groups may be added to the solution with a catalyst to form a mixture. The mixture may then be reacted at a predetermined temperature (e.g., ranging about 60° C. to about 150° C.) for a predetermined time (e.g., ranging from about 0.5 hours to about 20 hours). The product of the reaction can be dissolved in another suitable solvent and stirred at about 60-90° C. for about 0.5-1 hour to form the hydrogel.

In another example, the selected water soluble polymer may be dissolved in a first solvent to form a first solution. The ureido-pyrimidinone-containing pendant groups may be dissolved in a second solvent (which is the same as or different than the first solvent) to form a second solution. At least some of the first solution is mixed with at least some of the second solution to form a mixture. The ratio of first solution to second solution can be from 10:1 to 1:1. The mixture may then be stirred and cured at a predetermined temperature (e.g., ranging about 60° C. to about 150° C.) for a predetermined time (e.g., ranging from about 0.5 hours to about 20 hours). In some examples, additional processing may be included, in which the solvent is exchanged for water.

Several specific examples of the method will be described in more detail in the Example Section.

The graft density of ureido-pyrimidinone may be controlled by changing the feed ratio of the ureido-pyrimidinone-containing pendant group to the water-soluble polymer. Controlling the graft density enables the multi-functionalized polymer to form the robust hydrogel. $^1$H NMR of the multi-functionalized polymer may be carried out to confirm the structure, and the density of substitution (DS, number of ureido-pyrimidinone units per 100 repeating units) may be estimated by calculating the ratio of the areas under the characteristic peaks. In some examples, the hydrogel forms when the density of ureido-pyrimidinone is 8.1 or less. Polymers with too high of an ureido-pyrimidinone graft density have poor water solubility and thus are not suitable for hydrogel preparation.

Figure 1B:
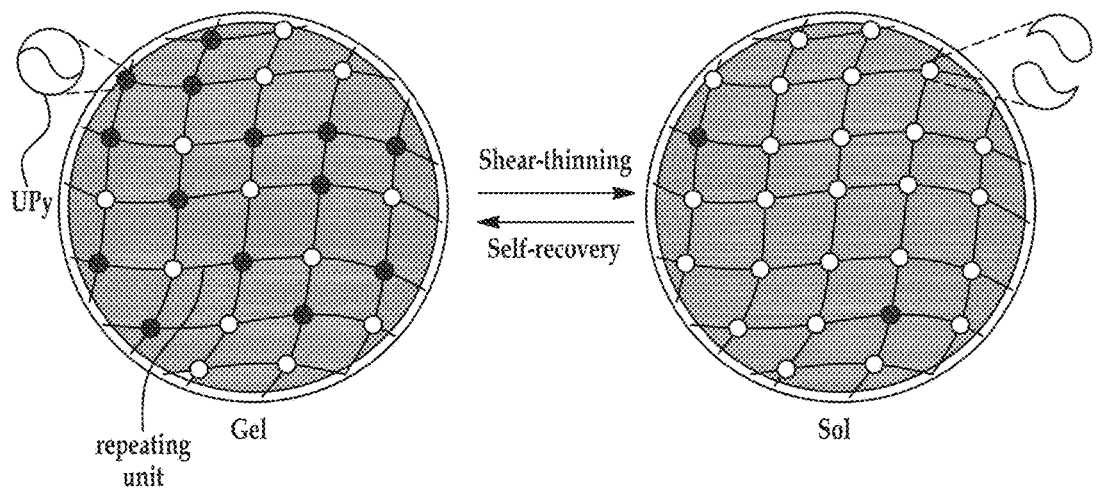
FIG. 1B is a schematic illustration of an example of the modified water soluble polymer and its shear-thinning and self-recovery properties.

With the appropriate ureido-pyrimidinone graft density, the water-soluble polymer disclosed herein may form a hydrogel. The hydrogel network formation is through the ureido-pyrimidinone (UPy) hydrogen bonds (see the gel in FIG. 1B). The hydrogel may be loaded into a syringe, and subsequently injected through a needle. The hydrogel behaves like a liquid under the shear stress during injection and solidifies instantly after the injection (shear thinning behavior). An example of these behaviors is shown in FIG. 1B, illustrating the dissociation of the ureido-pyrimidinone and the shear-thinning of the hydrogel when exposed to shear stress ranging from 10 Pa to 1 kPa, and illustrating the association of the ureido-pyrimidinone and self-recovery of the hydrogel upon removal of the shear stress.

Different shapes of the hydrogel may be fabricated by injecting them into differently shaped molds.

The hydrogel may be dyed or may be transparent. Any suitable dye may be used, and it may be added directly to the hydrogel.

When the hydrogels are to be used for drug/protein delivery, the drugs or proteins may be encapsulated in the hydrogel. This may be accomplished by dissolving the drug or protein in a suitable solvent and adding the dissolved drug or protein into the hydrogel solution before solidification. The amount of the drug-containing solution is usually below ⅓ of the total hydrogel volume.

Cells may also be incorporated into the hydrogels. Before the hydrogel is completely set, the cell (typically in a suitable medium) may be added to the hydrogel and mixed therein.

To further illustrate the present disclosure, examples are given herein. It is to be understood that these examples are provided for illustrative purposes and are not to be construed as limiting the scope of the present disclosure. Throughout the Example Section, ureido-pyrimidinone will be referred to as "UPy."

EXAMPLES

Example 1

Synthesis and Preparation of Dextran-Ureido-Pyrimidinone (DEX-Upy) Hydrogels

Figure 2:
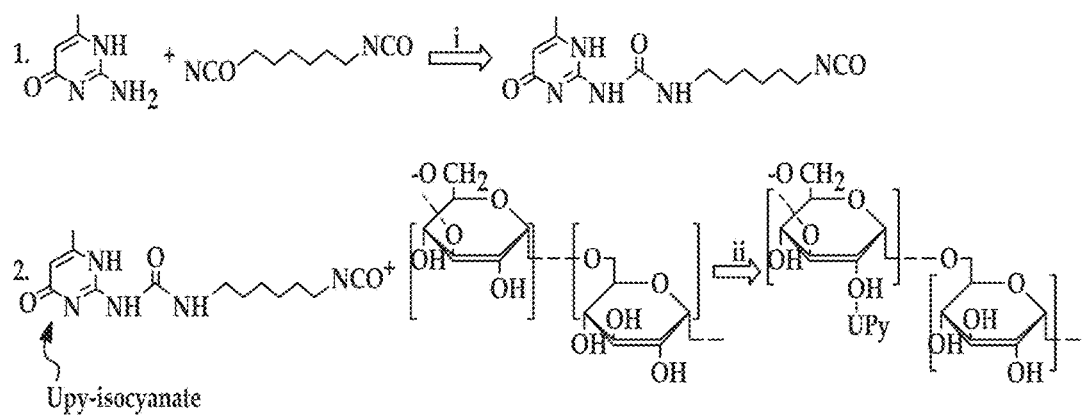
FIG. 2 illustrates the synthesis steps in an example of the method for forming a dextran-ureido-pyrimidinone (DEX-Upy) hydrogel.

To synthesize DEX-UPy polymer hydrogel, ureido-pyrimidinone was grafted onto the dextran backbone through the reaction of an isocyanate group with the hydroxyl groups of the glucose units. The reactions are shown in FIG. 2.

At the outset, 2-amino-4-hydroxy-6-methylpyrimidine (11.2 g, Sigma) was added into 100 ml 1,6-hexanediisocyanate (Sigma) and heated to 100° C. (shown at i) for 18 hours (reaction 1 in FIG. 2). Then, 1000 ml pentane (Sigma) was poured into the reaction solution and stirred with a magnetic bar to wash the unreacted hexanediisocyanate. The product was filtered and washed for another 5 times with pentane. The collected white powder (UPy-isocyanate) was dried under vacuum overnight. To synthesize the UPy grafted dextran, the dextran (2 g, MW 70,000) was dissolved in 70 ml anhydrous dimethyl sulfoxide (DMSO, Sigma) under nitrogen atmosphere with magnetic stirring, followed by the addition of UPy-isocyanate (0.4 g) and dibutyltin dilaurate (DBTDL, 0.586 ml, Sigma) (ii in FIG. 2). The reaction was carried out at 120° C. for 16 to 18 hours (ii in FIG. 2). The resulting solution was poured into isopropanol (700 ml, Fisher Scientific) for precipitation for 3 times. The powder was dried in vacuum overnight and re-dissolved in water. The aqueous solution was frozen in a freezer and lyophilized for 3 days.

To fabricate hydrogels, about 100 mg of the DEX-UPy polymer was dissolved in 900 µl sterile PBS (pH 7.4) at around 70° C. for 1 hour under magnetic stirring. Afterwards, the solution was loaded into a syringe and injected into a polydimethylsiloxane (PDMS) mold. For rheological property measurement, the hydrogel was put in a refrigerator at 4° C. overnight to allow for complete gelation.

Figure 3:
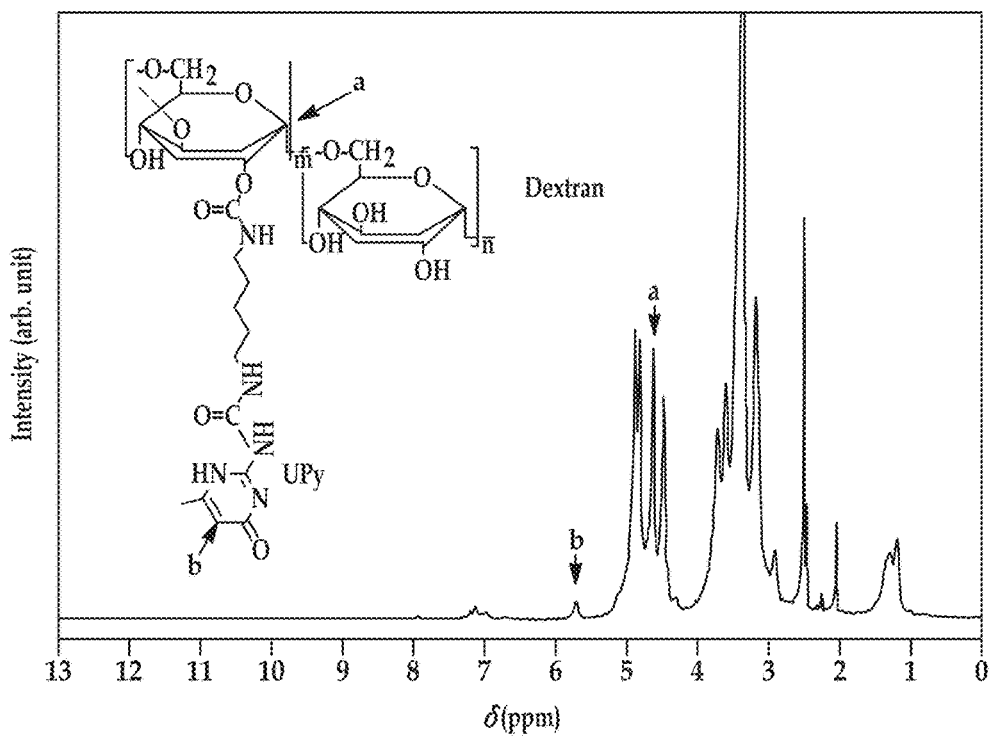
FIG. 3 is a graph depicting the $^1$H NMR characterization of an example DEX-Upy hydrogel having a density of substitution (DS) of 5.5 and a concentration of 10% (w/w) in dimethyl sulfoxide (DMSO)-d6.

The graft density of UPy can be controlled by changing the feed ratio of UPy to dextran. 1H NMR was carried out to confirm the structure of the DEX-UPy (FIG. 3). The density of substitution (DS, number of UPy units per 100 glucose units) was estimated by calculating the ratio of the areas under the characteristic peaks. In this example, $^1$H NMR characterization was carried out using a Varian MR400 (Cobalt) Spectrometer. $CDCl_3$ was used as the solvent for UPy-isocyanate and DMSO-d6 for DEX-UPy. The multi-functionalized polymer (DEX-UPy) could form a robust hydrogel when the density of UPy was sufficiently high. For example, DEX-UPy-2 (DS 5.5, 10% w/w) could be dissolved in water at elevated temperature (around 70° C.) and form a stable hydrogel after being cooled down to room temperature, while pure dextran and DEX-UPy with a very low graft density (DEX-UPy-1, DS 2.8) formed clear solutions under the same conditions. Polymers with too high an UPy graft density (DS≥8.1) have poor water solubility and thus could not be used for hydrogel preparation. With the appropriate UPy graft density, the DEX-UPy polymer formed a hydrogel, was loaded into a syringe and subsequently injected through a 26G needle. The hydrogel behaved like a liquid under the shear stress during injection and solidified instantly after the injection, which is evidence of its shear thinning behavior.

Figure 4:
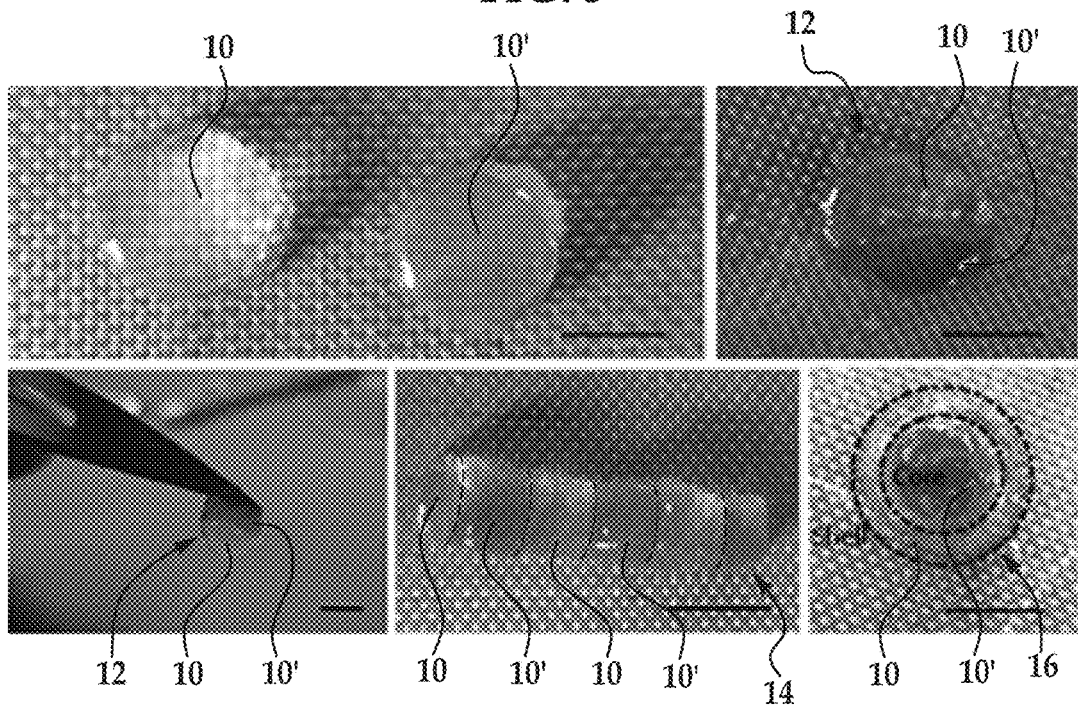
FIG. 4 includes black and white photographs of several examples of the DEX-Upy hydrogels (DS 5.5, 10% w/w), including separate undyed and rodamine dyed hydrogels (top left), and self-integrated hydrogels in different forms, such as a cylinder with two halves (top right and bottom left), a rod with alternating hydrogels (bottom center), and a core-shell structure (bottom right) (scale bar=5 mm)

To illustrate the self-integration capacity, the hydrogel disks were cut into different parts with a blade and were subsequently brought together manually (e.g., top left image in FIG. 4). One of the hydrogels was dyed with rodamine (10', see FIG. 4), and another of the hydrogels was left its original color (10, see FIG. 4) to show the interfaces between these hydrogel pieces. The hydrogel 10, 10' was found to integrate within minutes when the fresh surfaces were brought to contact with one another. As illustrated in FIG. 4, different patterns could be achieved, such as a cylinder 12 with two halves (where each half is one of the hydrogels 10, 10'), a rod 14 of joined discs (where each disc is one of the hydrogels 10, 10'), and an integrated cylinder 16 consisting of a core (formed of hydrogel 10') and a shell (formed of hydrogel 10). The photographs in FIG. 4 were taken 2 minutes after the hydrogels 10, 10' rejoined one another.

Rheological Measurements of Shear-thinning and Recovery of DEX-Upy Hydrogels

Figure 5A:
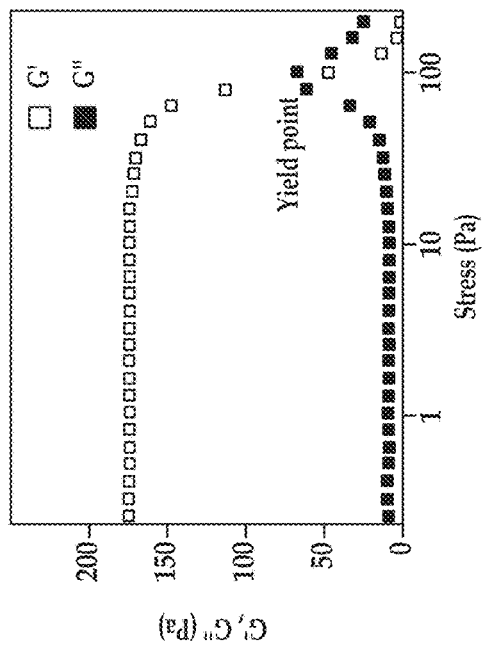
FIGS. 5A through 5D are graphs illustrating the rheological properties of different hydrogels, where

In order to quantify the mechanical properties associated with shear-thinning and the subsequent recovery, the rheological properties of the hydrogels were measured using an AR2000 rheometer (TA instruments, United States). Parallel plates with 40 mm diameter were used for all the tests. The gap distance between the plates was 0.4 mm. A constant stress of 0.1 Pa was applied for the frequency spectrum measurement (FIG. 5A, discussed below). For measurements other than frequency spectrum, a constant 1 rad/s angular speed was used. The high stress and low stress used in the shear-thinning (FIG. 5B) and self-recovery (FIG. 5C) experiments were 100 Pa and 0.1 Pa, respectively. Self-recovery of the modulus was validated after 3 cycles of high and low stress. For the temperature stability test (FIG. 5D, discussed below), the modulus during the heating process was measured with a heating rate of 2° C./min from room temperature (~18° C. to about 22° C.) to about 70° C.

FIGS. 5A through 5D are graphs illustrating the rheological properties of the hydrogels. In FIG. 5A, the frequency spectra of the dynamic moduli (storage modulus G', loss modulus G") of DEX-UPy (DS 5.5) hydrogels with concentrations of 12.5% and 10% w/w is shown, where a constant stress of 0.1 Pa was applied. The hydrogel made of the 10% (w/w) DEX-UPy (DS 5.5) polymer solution had a storage modulus of 170 Pa, whereas the hydrogel made of the same polymer with the concentration of 12.5% (w/w) had a storage modulus of 700 Pa. These results illustrate the non-linear relationship between the polymer concentration and the mechanical properties of the polymer.

Figure 5B:
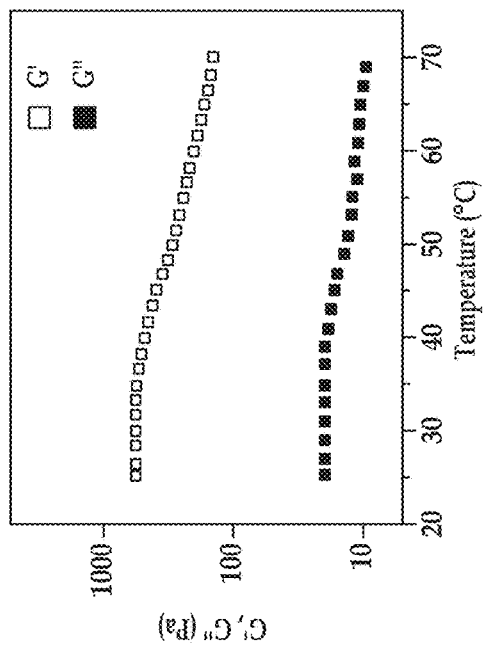

In FIG. 5B, the dynamic modulus of the 10% (w/w) hydrogel (DS 5.5) under increasing stress is depicted. For this example, a shear force was applied to the hydrogel, mimicking the change from the statically stored gel to the mechanical injection of the gel from a syringe. The hydrogel yielded at a critical shear stress level and lost its mechanical integrity, which corresponds to the state of the hydrogel being injected through a needle. At the critical shear stress level, the storage modulus (G') fell below the loss modulus (G"). This phenomenon is a demonstration of the shear-thinning property.

Figure 5C:
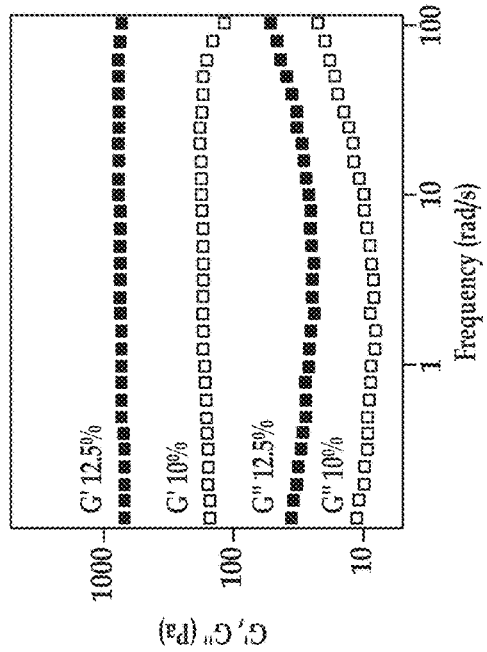

Furthermore, cyclic high and low stresses ($\sigma_H$ and $\sigma_L$, respectively) were applied to the hydrogel. FIG. 5C depicts the dynamic modulus of the 10% (w/w) hydrogel (DS 5.5) under cyclic high (100 Pa) and low (0.1 Pa) stresses. Under the low stress, DEX-UPy behaved like a gel. More particularly, at the low stress level, the gel remained stable and the G' was higher than G". At the high stress level, the gel changed into a liquid-like state (sol) with the G' lower than G". The gel state was instantly (within seconds) recovered after the removal of the high stress. The hydrogel could be shear-thinned and recovered for many cycles without significant loss of the mechanical properties.

Figure 5D:
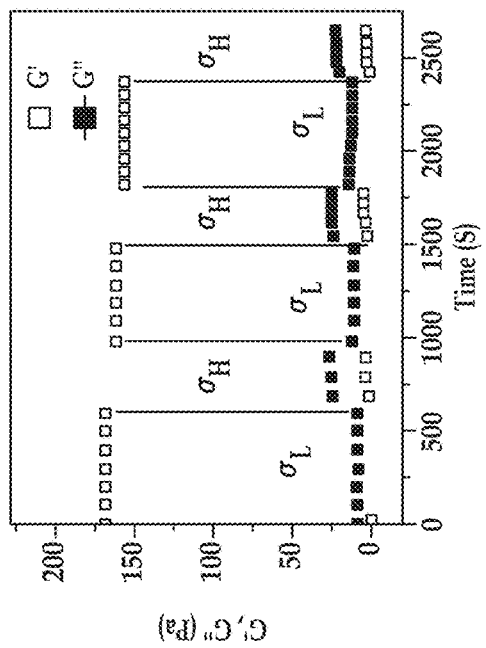

The stability of the 10% (w/w) hydrogel (DS 5.5) upon heating was validated by measuring the change of the rheological properties against the temperature. FIG. 5D depicts the change of the dynamic modulus of the 10% (w/w) hydrogel (DS 5.5) with temperature. The hydrogel was softened while being heated at a rate of 2° C./min from room temperature (i.e., the modulus decreased upon heating), but it maintained the gel state even at 70° C.

In vitro Degradation/Erosion of DEX-Upy Hydrogels

The DEX-UPy hydrogels degrade mainly through a physical erosion process, during which the hydrophilic polymer gel disassociates and diffuses to the aqueous environment. To test the degradation/erosion, the hydrogels made of the 10% (w/w) DEX-UPy (DS 5.5) polymer solution and of the 12.5% (w/w) DEX-UPy (DS 5.5) polymer solution were loaded into syringes and stored in a refrigerator at 4° C. overnight. The hydrogels were then injected into 1.5 ml eppendorf tubes. For every 100 mg hydrogel in a tube, 1 ml PBS (pH7.4) was added. The tubes were incubated on a shaker with a shaking speed of 100 rpm in an incubator at 37° C. At each predetermined time point, 3 samples were collected and freeze-dried. The dry weights were measured on a balance, accurate to 0.1 mg. The dry weight loss was calculated to quantify the erosion. The results are shown in FIG. 6.

Figure 6:
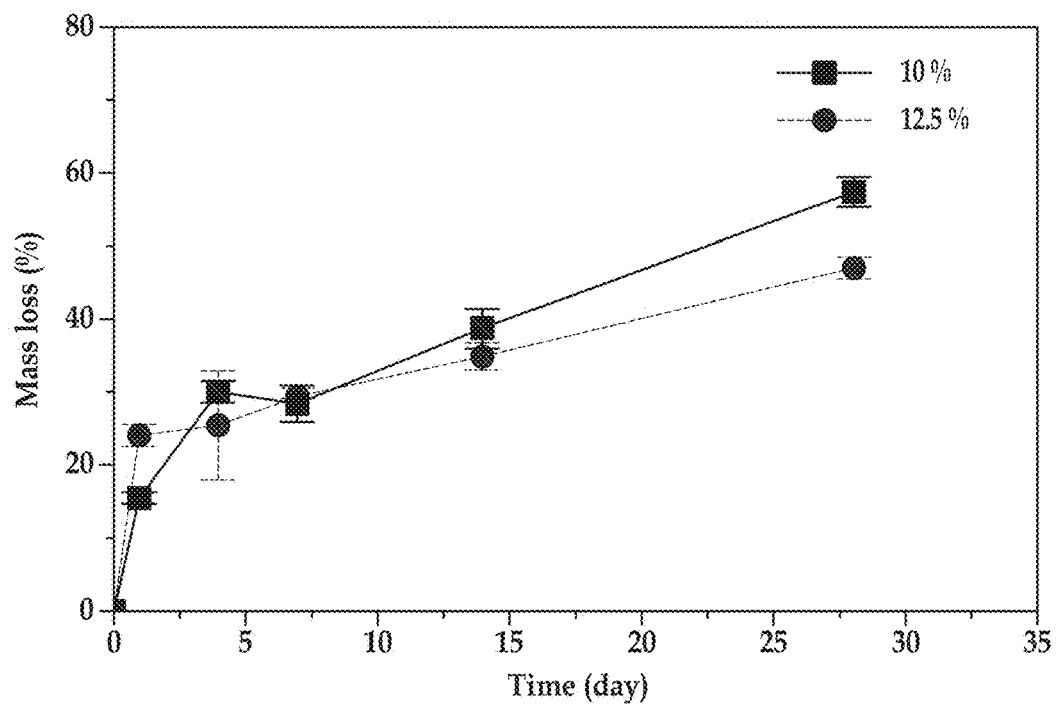
FIG. 6 is a graph illustrating the in vitro degradation of DEX-Upy hydrogels (DS 5.5) with concentrations of 12.5% and 10% w/w in phosphate buffered saline (PBS) at 37° C.

The data in FIG. 6 show that hydrogel with a concentration of 10% and a UPy content of 5.5% (i.e., 10% (w/w) DEX-UPy (DS 5.5)) lost 57% mass in four weeks, while the hydrogel with a concentration of 12.5% and the same UPy content (i.e., 12% (w/w) DEX-UPy (DS 5.5)) degraded slower, and lost 47% mass in the same time period. The degradation profiles of these hydrogels may be suitable for engineering many tissue types, where the need for a temporary template is typically weeks to months.

In vitro Drug Release of DEX-Upy Hydrogels

Drugs or proteins can be encapsulated in the hydrogel and released over time (e.g., in durations from days to months), which is dependent on the size and characteristics of the drug or protein. To test the drug release, the DEX-UPy powder was dissolved into PBS to prepare a hydrogel with a concentration of 11% (w/w). Doxycycline (DOXY, which is a model drug of small molecules) and bovine serum albumin (BSA, which is a model protein) were pre-dissolved in PBS, and were respectively added into samples of the DEX-UPy solution before they solidified. The final concentration of the hydrogel was 10% with a drug concentration or protein concentration of 0.5% of the total weight. The hydrogels were loaded into respective syringes. 60 μg hydrogels were injected to the bottom of a 1.5 ml Eppendorf tube. After that, 1 ml PBS was added to the tube. Five hundred μl of the solution was sampled at each time point and 500 μl fresh PBS was added.

Figure 7:
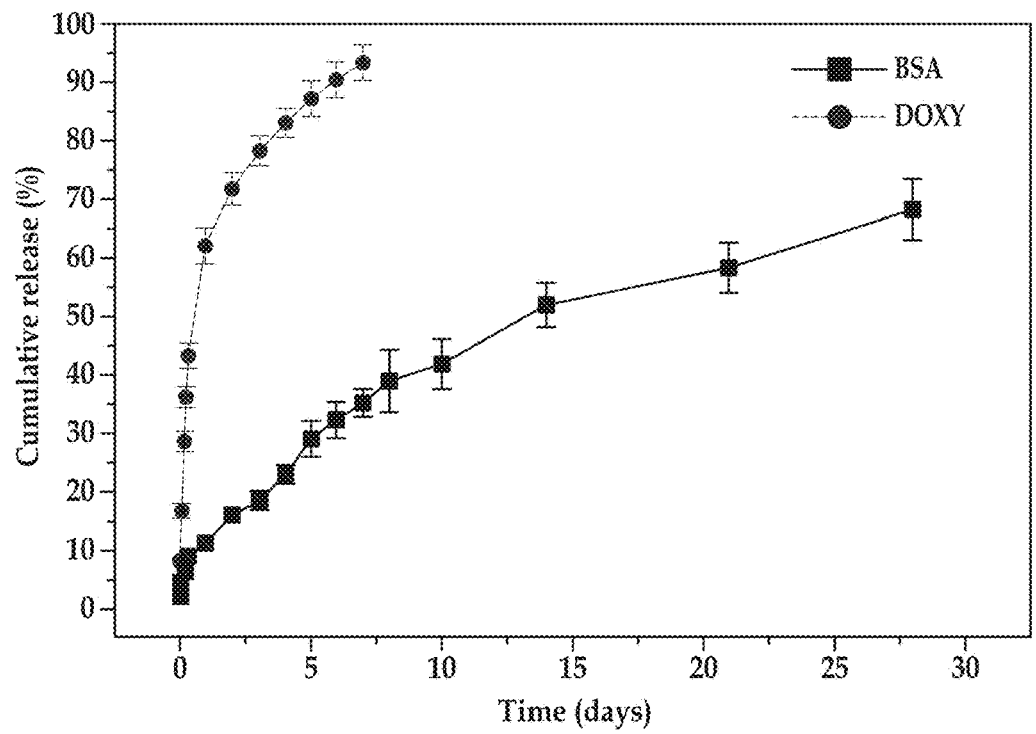
FIG. 7 is a graph illustrating the in vitro release of doxycycline (DOXY) and bovine serum albumin (BSA) from DEX-Upy hydrogels (DS 5.5) with a concentration of 10% w/w in PBS at 37° C.

The release results are shown in FIG. 7. The concentration of the released DOXY was measured by quantifying the UV absorbance at 273 nm using UV-spectrophotometer (HITACHI, U-2910). The concentration was determined using a pre-established standard concentration intensity curve. As illustrated, DOXY was nearly completely released in vitro during the first week. The concentration of released BSA was determined using a Micro BCA™ Protein Assay Kit (Thermo Scientific) following the standard procedure. BSA was released for more than a month, and there was no significant burst release. Around 10% of BSA was released during the first day. A nearly linear release was achieved for BSA during the entire experimental duration of 4 weeks. This sustained release profile for proteins/growth factors is highly desired for tissue engineering applications.

Cell Encapsulation and Biocompatibility with DEX-Upy Hydrogels

Different types of cells, including chondrocytes and bone marrow stem cells, were encapsulated and cultured in the DEX-Upy Hydrogels.

Articular cartilage was obtained from the femoral heads and knees (condyles and patellar grooves) of four-week-old New Zealand white rabbits (Harlan Sprague Dawley, Michigan, USA) under sterile conditions, stripped of any adherent connective tissue, and minced into small pieces. After digestion with 0.2% collagenase type II for 16 hours, the primary chondrocytes were collected and were passaged for two times. The chondrocytes were cultured in a high glucose DMEM (Gibco) medium containing 20% (v/v) fetal bovine serum (FBS). Rabbit bone marrow-derived cells (BMSCs) were collected via aspiration from the femoral bone marrow using an 18-gauge syringe needle, collecting 10 ml of marrow into 1000 U of heparin. The marrow was filtered through a cell strainer to exclude fatty tissues and blood clots, and centrifuged at 600 rpm for 30 minutes. Rabbit BMSCs were collected and cultured in 75-cm² flasks in low-glucose a-MEM (Gibco) containing 10% fetal bovine serum (Gibco).

Before being dissolved in water, the DEX-UPy powders were sterilized by autoclaving at 121° C. for 25 minutes. Hydrogels (11% (w/w)) were prepared in PBS as previously described. After the hydrogel solution was cooled down to room temperature, chondrocytes or BMSCs in a medium were added and mixed while stirring, diluting the final concentration of the hydrogels to 10% (v/v). The cell density was 1 million/ml. To better visualize the cells, the chondrocytes and BMSCs were labeled with ER-Tracker™ Green (BODIPY® FL Glibenclamide, Invitrogen) and MitoTracker® Red CMXRos (Invitrogen), respectively, following the standard procedure.

The cell-hydrogel mixtures were loaded into syringes and injected into a 12-well culture plate, followed by adding DMEM medium (Gibco). The culture medium was changed twice a week.

Confocal images (not shown) were taken, and the images showed the uniform distribution of both types of cells. A live-dead assay (results also not shown) confirmed that both chondrocytes and BMSCs maintained a high viability in the hydrogel as examined after in culture for two weeks, indicating that the DEX-UPy hydrogel is highly biocompatible with mammalian cells.

Preparation of Self-Integrated Cell-DEX-Upy Hydrogel Constructs

A self-integrated scaffold for bone-cartilage-complex tissue engineering was prepared. Chondrocytes (for cartilage formation) and BMSCs plus bone morphogenetic protein 2 (BMP-2, for bone regeneration) were encapsulated in two portions of the hydrogel separately, as described in the previous section except the final cell density was 10 million/ml. The chondrocyte-containing hydrogel is labeled 22 in FIG. 8A and the BMSCs plus BMP-2-containing hydrogel is labeled 24 in FIG. 8A. To better visualize the cells, the chondrocytes and BMSCs were labeled with ER-Tracker™ Green (BODIPY® FL Glibenclamide, Invitrogen) and MitoTracker® Red CMXRos (Invitrogen), respectively. Then, the cell-containing hydrogels were injected into the two sides of a disk-shaped PDMS mold (labeled 20 in FIG. 8A, with the inner diameter of 4 mm, outer diameter of 7 mm, and thickness of 2 mm) separated by a baffle film (labeled 18 in FIG. 8A, formed of polytetrafluoroethylene, i.e., TEFLON®) in the middle. The film 18 was subsequently removed to allow the integration of the chondrocyte-containing hydrogel and the BMSCs-containing hydrogel. To ensure sufficient time for complete gelation, the culture plate was put in the incubator for 60 minutes before adding the culture medium. The integrated hydrogel was observed under a confocal microscope (Olympus Fluoview 500) after being cultured in a DMEM medium (Gibco) for 2 days. The two components self-integrated immediately after the baffle film was removed.

Figure 8B:
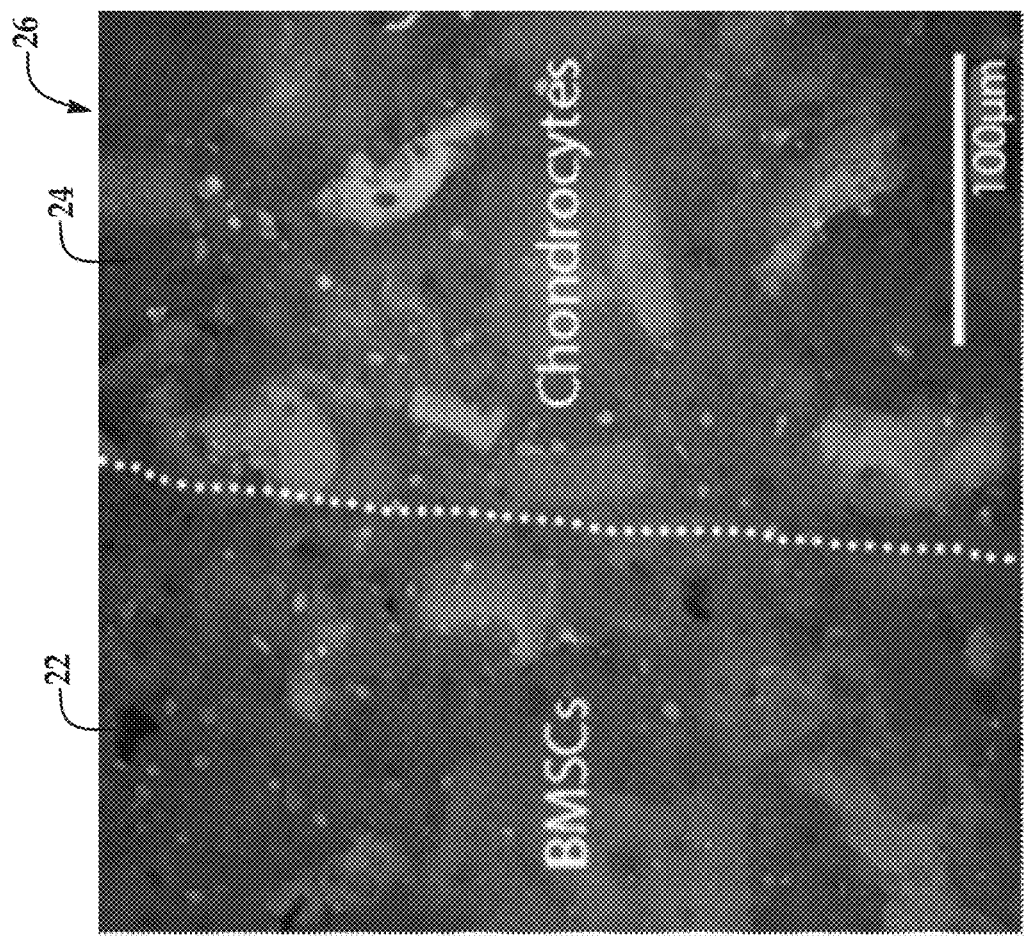
FIG. 8B is a black and white confocal image of the cells encapsulated in the hydrogel construct, where the chondrocytes were stained green and the BMSCs were stained red.
Figure 8A:
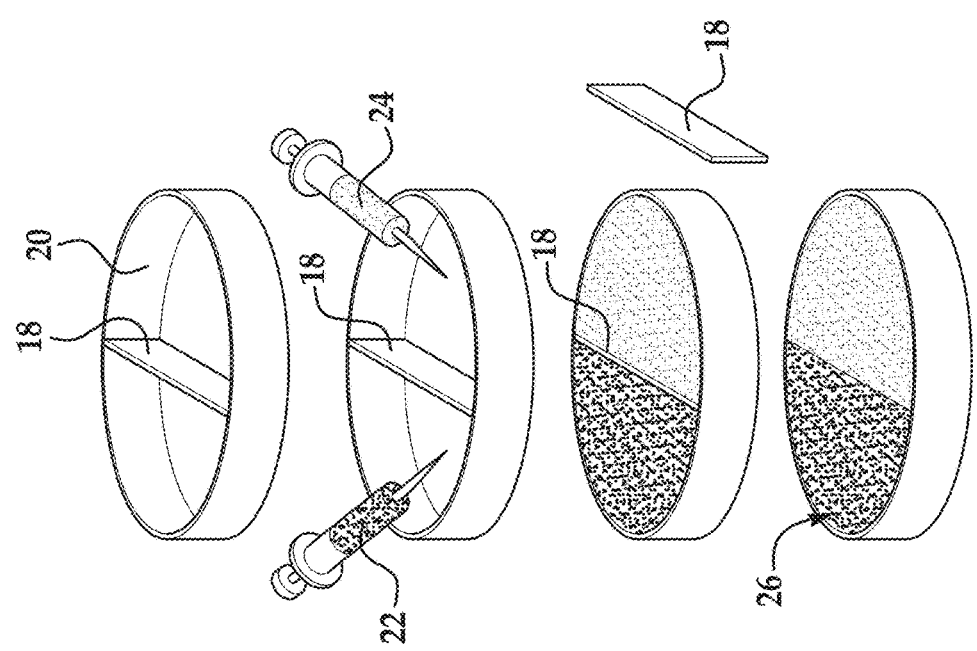
FIG. 8A is a schematic illustration of the preparation of a self-integrated hydrogel construct encapsulating chondrocytes and Rabbit bone marrow-derived cells (BMSCs)

FIG. 8A schematically illustrates the PDMS mold 20, the injection of the cell-containing hydrogels 22, 24 into baffle film 18-separated sides of the PDMS mold 20, the removal of the baffle film 18, and the integration of the two hydrogels 22, 24 into an integrated cell-gel construct 26. The black and white confocal image of FIG. 8B shows the clear interface between the chondrocyte-containing hydrogel 24 and the BMSCs plus BMP-2-containing hydrogel 22 in the integrated cell-gel construct 26, mimicking the intimate bone-cartilage interface in the joints. No external intervention was necessary to integrate the two cell-loaded gels to construct the bone-cartilage complex.

Subcutaneous Implantation of the Self-Integrated Hydrogel Constructs in Mice

All animal procedures were carried out under the guidelines of the Institutional Animal Care and Use Committee of the University of Michigan. Nude mice (6-8 weeks old, NU/NU, Charles River Laboratories USA) were anaesthetized with 2.5% isoflurane in balanced oxygen. Three groups of cell-gel constructs (chondrocytes only, BMSCs/BMP-2 only, and self-integrated hydrogel with the two cell types on two sides) were fabricated using the same methods as described above. The cell density was 10 million/ml for both chondrocytes and BMSCs in all constructs. The concentration of BMP-2 was 50 µg/ml.

The cell-gel constructs were subcutaneously implanted in mice to evaluate the potential of engineering osteochondral complex using the self-integrating hydrogel disclosed herein. The respective cell-gel constructs were implanted into subcutaneous pockets and each mouse received four implants. The implants were randomly arranged in nude mice, with four specimens per group. The constructs were collected after eight weeks and the fibrous capsules were removed.

The samples were used for histological examinations. More specifically, the implanted specimens were collected and fixed in 10% buffered formalin at 4° C. for 8 hours. The fixed tissues were then immersed in Tissue-Tek™ CRYO-OCT compound (Sakura Finetek USA, Inc.) and subsequently stored at −80° C. overnight. The specimens were cryosectioned at a thickness of 10 µm and stained using Alcian blue and/or Alizarin red. Positive staining of mineralized tissue (Alizarin red, for bone) and sulfated glycosaminoglycan (Alcian blue, for cartilage) in the histological sections validated the formation of cartilage and bone within the single cell groups respectively (shown in black and white in FIGS. 9A and 9B). The results demonstrate the capability of the hydrogels disclosed herein in supporting the growth of both bone and cartilage tissues.

The self-integrated osteochondral implants were stained using both Alcian blue and Alizarin red (shown in black and white FIG. 9C). Both bone and cartilage tissues were identified within their spatially defined regions. The BMSCs/BMP-2 side (left side in FIG. 9C) displayed positive staining for bone, while the chondrocytes side (right side in FIG. 9C) showed positive staining for cartilage only. The regenerated bone and cartilage tissues were intimately integrated as shown in the magnified image (shown in black and white FIG. 9D). Such seamless bone and cartilage integration is desirable in joint function.

The volumes of bone and cartilage tissues were quantified using 10 sections from 4 different samples. The results are shown in FIG. 9E. The results show that cartilage occupied larger volume (≈70%) than bone (≈30%). The difference in the regenerated tissue volume between the two types of tissues is discussed below.

The results in FIGS. 9C-9E confirmed that a bone-cartilage tissue complex, which resembles the native tissues, was formed after 8 weeks of implantation, and also that seamless integration between the two types of tissues was achieved. As such, the hydrogel disclosed herein represents a new class of scaffolding materials and has great potential for engineering various tissue complexes.

Example 2

Synthesis and Preparation of Transparent Dextran-Ureido-Pyrimidinone (DEX-Upy) Hydrogels Amination may be used when a light yellow color is desirable for the hydrogel. In an example, amination of the dextran would involve first dissolving the dextran (10 mmol sugar unit, MW 70,000) in 50 mL of anhydrous dimethyl sulfoxide (DMSO) followed by the addition of 1,1'-carbonyldiimidazole (7.5 mmol). The reaction may be carried out under a nitrogen atmosphere at room temperature for about 4 hours. 1,6-Hexanediamine (20 mmol) is then added to the solution, and then the solution is stirred overnight at room temperature. The reaction product is subsequently purified by dialysis (MW cut-off=6000-8000 Da) against de-ionized water. Purified aminated dextran is obtained after lyophilization for 2 days.

However, a transparent DEX-UPy hydrogel can be prepared without having to first perform amination of the dextran.

To form the transparent DEX-UPy hydrogel, carbonyldiimidazole (CDI) activation of methyl-isocytosine is initially performed. This involved suspending 2-Amino-4-hydroxy-6-methypyrimidine (8 mmol) and CDI (10.4 mmol) in 40 ml DMSO, heating the suspension to 80° C., and maintaining the suspension at that temperature for 1 hour. The reaction mixture was cooled down to room temperature, and 200 ml acetone was added. The precipitate was filtered and dried in vacuum overnight.

Dextran (0.5 g) was dissolved in 15 ml DMSO, while CDI-activated methyl-isocytosine (0.06g) was dissolved in DMF under mild heating. The solution of DMF was then added into DMSO under stirring. The reaction was carried out at room temperature for 20 hours. The reaction product was subsequently purified by dialysis against de-ionized water for 2 days and lyophilized for 3 days.

While the results are not shown, two separate transparent hydrogels were able to self-integrate.

Example 3

Figure 10:
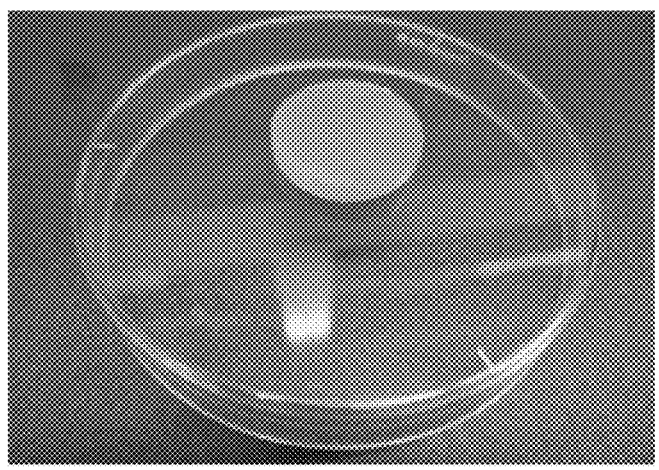
FIG. 10 is a black and white photograph of a hydrogel formed with polyvinyl alcohol and ureido-pyrimidinone.

Synthesis and Preparation of Polyvinyl Alcohol-Ureido-Pyrimidinone (PVA-Upy) Hydrogels PVA (1 g) was first dissolved in 10 ml anhydrous dimethyl sulfoxide (DMSO) with a weight concentration of 10%. To accelerate the dissolution, moderate heat or sonication was used. 0.4 g UPy-isocyanate was separately dissolved in 10 ml DMSO. These two solutions were mixed according to predetermined ratio, followed by the addition of one drop DBTDL as a catalyst. The feed ratio (PVA:UPy) in terms of weight were 2:0.4, and the PVA concentration was 4.8%. The mixed solution was stirred and then cured at 100° C. for 3 hours. The gel was submersed in de-ionized water for 24 hours to replace the DMSO with water and wash the unreacted molecules away. FIG. 10 is a photograph of an example of the prepared PVA-UPy hydrogel.

Example 4

Synthesis and Preparation of Chitosan-Ureido-Pyrimidinone (CHI-Upy) Hydrogels

Figure 11:
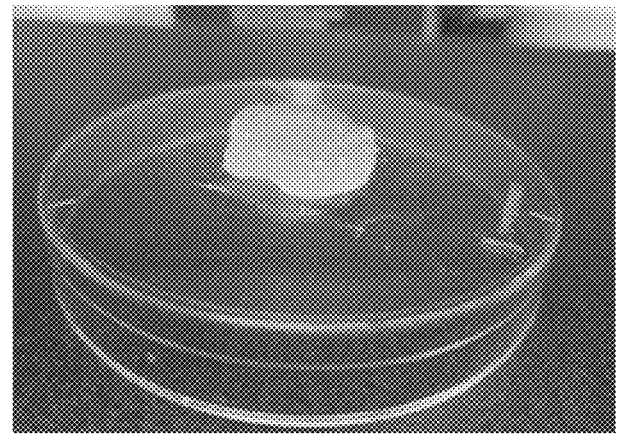
FIG. 11 is a black and white photograph of a hydrogel formed with chitosan and ureido-pyrimidinone.

5% chitosan solution was prepared by dissolving 100 mg chitosan in 1.9 ml water/lactic acid (20:1) solution. UPy-isocyanate was separately dissolved in DMSO. To fabricate the gels, 400 µl chitosan solution was diluted by 1.6 ml UPy-isocyanate solution with a weight ratio of 2:0.8. One drop of DBTDL was added into the mixed solution. After sufficient stirring, the solution was cured at 100° C. for 1 hour. The gel was solvent exchanged with de-ionized water for 24 hours. FIG. 11 is a photograph of an example of the prepared CHI-UPy hydrogel.

Example 5

Synthesis and Preparation of Hydroxyethyl Cellulose-Ureido-Pyrimidinone (HEC-Upy) Hydrogels To synthesize the UPy grafted HEC, 1 g HEC (typically $M_v$=90000, Aldrich) was dissolved in 100 ml anhydrous DMSO under nitrogen atmosphere with magnetic stirring, followed by the adding of UPy-isocyanate (0.2 g) and three drops of DBTDL. The reaction was carried out at 120° C. for 16 hours. The resulting solution was precipitate with acetone (1000 ml, Fisher Scientific). The powder was dried in vacuum and re-dissolved in water. The aqueous solution was frozen in freezer and lyophilized for 3 days.

Figure 12:
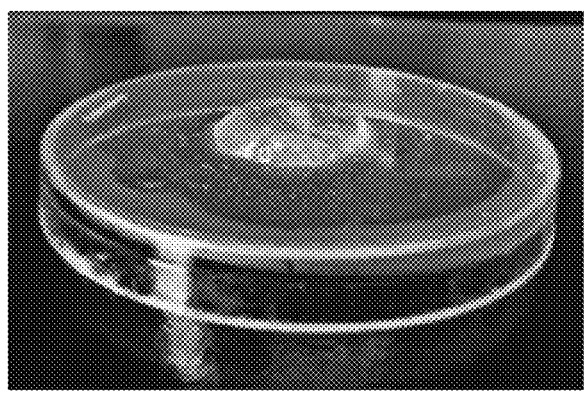
FIG. 12 is a black and white photograph of a hydrogel formed with hydroxyethyl cellulose and ureido-pyrimidinone.

To fabricate the hydrogel, 50 mg of the HEC-UPy polymer was dissolved in PBS (950 µl) at around 70° C. with magnetic stirring. The solution was put in 4° C. freezer overnight. The hydrogel formed is shown in FIG. 12.

Examples of the hydrogel disclosed herein are injectable and self-integrating. The self-integration occurs within minutes when pieces of the hydrogel are put into contact with one another. This is unlike the self-integration observed in polyethylene glycol (PEG) polymers functionalized with ureido-pyrimidinone at the chain ends, because this integration can take from hours to days due to the slow kinetics involved. In contrast, the modified water soluble polymers disclosed herein contain large numbers of the multi-hydrogen-bond units (UPy) attached along the polymer backbone. As demonstrated in the Examples, stable hydrogels can be formed from UPy interactions without relying on additional hydrophobic interactions or the urea segments as in the PEG-UPy hydrogel. Therefore, the gelation and re-adhesion (self-integrating) occurs in a much shorter time period (e.g., a few minutes).

Furthermore, the DEX-Upy hydrogels disclosed herein are substantially more stable than the hydrophobically modified PEG hydrogel, as indicated by their erosion ("degradation") profiles. The PEG hydrogel has been shown to fully erode and release the cargo in vitro within 24 hours, while the DEX-UPy hydrogel tested in Example 1 maintained the integrity for longer than a month. Moreover, the DEX-UPy hydrogels were shown to be capable of releasing protein drugs nearly linearly for longer than a month, which should greatly enhance the therapeutic efficacy of the drugs.

The example hydrogels disclosed herein, which combine a biocompatible polymer and multiple UPy units, are injectable and can rapidly self-integrate without using any external stimulus, thus preventing potential harm to the encapsulated cells or biomolecules. These properties are particularly beneficial to tissue engineering applications.

The self-integration characteristic of the hydrogels disclosed herein also enables the hydrogels to be used in engineer multi-tissue complexes. Regeneration of complex tissues is highly challenging because it requires a scaffold that integrates different cells/biomolecules in spatially defined regions. One example is the osteochondral defect, where tightly bounded bone and cartilage need to form simultaneously and be integrated seamlessly. The in vivo results illustrated in Example 1 validate the utility of the self-integrating hydrogel in such an occasion. In these results, the bone and cartilage tissues were distributed in opposite sides of the self-integrated construct, where BMSCs/BMP-2 and chondrocytes were initially encapsulated respectively. The histological results confirmed a good integration of two different tissues and they resembled the histoarchitectures of the native tissues. Moreover, based on quantitative analysis of the histology sections, it was found that cartilage occupied a larger volume than bone. Numerous studies have shown that co-culture of BMSCs with chondrocytes, either in mixed state or in close contact, would induce the differentiation of BMSCs to chondrocytes. It is believed that chondrocytes were induced from BMSCs at the interface region and therefore resulted in cartilage formation across the original boundary, leading to more cartilage than bone formation and the seamless integration between these two types of tissues. To generate equal volumes of bone and cartilage, a smaller initial volume of chondrocyte-containing hydrogel could be used.

Overall, the hydrogels disclosed herein are biocompatible, biodegradable and capable of releasing biomolecules sustainably.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from room temperature (~18° C. to about 22° C.) to about 70° C. should be interpreted to include not only the explicitly recited limits of about room temperature (~18° C. to about 22° C.) to about 70° C., but also to include individual values, such as 25° C., 34.5° C., 68° C., etc., and sub-ranges, such as from about 30° C. to about 65° C., from about 19° C. to about 59° C., etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A self-integrating hydrogel, consisting of
a water-soluble polymer, including:
a repeating unit containing at least one glucose unit; and
a pendant chain covalently attached to an oxygen atom of some of the repeating units, the pendant chain including ureido-pyrimidinone, wherein a density of substitution of the ureido-pyrimidinone is 8.1 or less.

2. The self-integrating hydrogel as defined in claim 1 wherein the hydrogel does not have a core-shell structure.

3. The self-integrating hydrogel as defined in claim 1 wherein the water-soluble polymer is a modified dextran.

4. The self-integrating hydrogel as defined in claim 1 wherein the water-soluble polymer is a modified cellulose and the repeating unit includes two β(1→4) linked D-glucose units.

5. The self-integrating hydrogel as defined in claim 1 wherein the pendant chain includes an isocyanate that links the ureido-pyrimidinone to the oxygen atom of the some of the repeating units.

6. The self-integrating hydrogel as defined in claim 1 wherein the pendant chain includes an activated ester, an epoxy group, or an acyl chloride group that links the ureido-pyrimidinone to the oxygen atom of the some of the repeating units.

7. A method for making the self-integrating hydrogel as defined in claim 1, the method comprising grafting a ureido-pyrimidinone-isocyanate to a hydroxyl group of some repeating units of a backbone of the water soluble polymer, each repeating unit containing the at least one glucose unit, thereby forming the pendant chain including the ureido-pyrimidinone-isocyanate.

8. The method as defined in claim 7, further comprising forming the ureido-pyrimidinone-isocyanate by reacting an isocyanate with 2-amino-4-hydroxy-6-methylpyrimidine.

9. The method as defined in claim 8, further comprising:
dissolving water soluble polymer in a first solvent to form a first solution;
dissolving the ureido-pyrimidinone-isocyanate in a second solvent to form a second solution;
mixing at least some of the first solution with the second solution to form a mixture;
adding a catalyst to the mixture under stirring;
curing the mixture at a predetermined temperature for a predetermined time to form the self-integrating hydrogel; and
exposing the self-integrating hydrogel to a solvent exchange process.

10. The method as defined in claim 7, further comprising controlling the density of substitution of ureido-pyrimidinone by changing a feed ratio of the ureido-pyrimidinone-isocyanate to the water-soluble polymer.

* * * * *